US009328190B2

(12) United States Patent
Iavarone et al.

(10) Patent No.: US 9,328,190 B2
(45) Date of Patent: May 3, 2016

(54) NON-TEXTILE POLYMER COMPOSITIONS AND METHODS

(75) Inventors: Charles Frank Iavarone, Crozet, VA (US); James Michael Lambert, Staunton, VA (US); Hong Liu, Waynesboro, VA (US); Sonia Menot, Ferney-voltaire (FR); Federica Maria Roberta Stoppa, Genthod (CH)

(73) Assignee: INVISTA North America S.a.r.l., Wilmington, DE (US)

( * ) Notice: Subject to any disclaimer, the term of this patent is extended or adjusted under 35 U.S.C. 154(b) by 620 days.

(21) Appl. No.: 12/559,114

(22) Filed: Sep. 14, 2009

(65) Prior Publication Data
US 2010/0063218 A1    Mar. 11, 2010

Related U.S. Application Data

(63) Continuation of application No. PCT/US2008/054942, filed on Feb. 26, 2008, and a continuation-in-part of application No. 11/654,753, filed on Jan. 18, 2007.

(60) Provisional application No. 60/759,853, filed on Jan. 18, 2006, provisional application No. 60/837,011, filed on Aug. 11, 2006, provisional application No. 60/865,091, filed on Nov. 9, 2006.

(51) Int. Cl.
| | |
|---|---|
| C09D 175/04 | (2006.01) |
| D06M 15/564 | (2006.01) |
| D06M 101/38 | (2006.01) |
| D06M 23/08 | (2006.01) |
| A61K 8/87 | (2006.01) |
| A61K 8/88 | (2006.01) |
| A61Q 19/00 | (2006.01) |
| A61Q 19/10 | (2006.01) |
| C08G 18/12 | (2006.01) |
| C08G 18/08 | (2006.01) |
| C08G 18/48 | (2006.01) |
| C08G 18/66 | (2006.01) |
| C08G 18/76 | (2006.01) |
| C11D 3/37 | (2006.01) |
| C11D 3/50 | (2006.01) |
| D06M 15/59 | (2006.01) |
| A61K 8/02 | (2006.01) |
| A61Q 1/12 | (2006.01) |

(52) U.S. Cl.
CPC .............. *C08G 18/12* (2013.01); *A61K 8/0241* (2013.01); *A61K 8/87* (2013.01); *A61K 8/88* (2013.01); *A61Q 19/00* (2013.01); *A61Q 19/10* (2013.01); *C08G 18/0823* (2013.01); *C08G 18/0861* (2013.01); *C08G 18/4854* (2013.01); *C08G 18/6692* (2013.01); *C08G 18/7671* (2013.01); *C09D 175/04* (2013.01); *C11D 3/3726* (2013.01); *C11D 3/505* (2013.01); *D06M 15/564* (2013.01); *D06M 15/59* (2013.01); *D06M 23/08* (2013.01); *A61K 2800/28* (2013.01); *A61K 2800/654* (2013.01); *A61Q 1/12* (2013.01); *D06M 2200/20* (2013.01)

(58) Field of Classification Search
CPC ............... C08G 18/12; C08G 18/4854; C08G 18/6692; C08G 18/0861; C08G 18/0823; C08G 18/7671; C08G 18/302; C08G 18/3228; A61K 8/0241; A61K 8/87; A61K 8/88; A61K 2800/28; D06M 15/564; D06M 15/59; D06M 2200/20; D06M 23/08; C11D 3/505; C11D 3/3726; C09D 175/04; A61Q 1/12; A61Q 19/00; A61Q 19/10
USPC .............. 524/591, 589, 70.1; 241/23; 528/71, 528/272
See application file for complete search history.

(56) References Cited

U.S. PATENT DOCUMENTS

| | | | |
|---|---|---|---|
| 2,975,128 A | | 3/1961 | Stott |
| 3,522,328 A | | 7/1970 | Caldwell |
| 3,686,069 A | | 8/1972 | Winkler |
| 4,645,131 A | * | 2/1987 | Hailey ............................ 241/23 |
| 4,732,934 A | | 3/1988 | Hathaway |
| 5,126,181 A | | 6/1992 | Figuly et al. |
| 5,280,088 A | | 1/1994 | Gambale |
| 5,879,596 A | * | 3/1999 | Roach ............................. 264/28 |
| 5,942,553 A | * | 8/1999 | Biesmans et al. ............... 521/99 |
| 6,107,444 A | * | 8/2000 | Bruneau et al. ............... 528/272 |
| 6,433,073 B1 | * | 8/2002 | Kantner et al. ............... 524/591 |
| 6,670,402 B1 | * | 12/2003 | Lee et al. ....................... 516/111 |
| 2006/0025740 A1 | * | 2/2006 | Osborn, III ......... A61F 13/2051 604/385.18 |

FOREIGN PATENT DOCUMENTS

| | | | | |
|---|---|---|---|---|
| GB | 871591 | | 3/1988 | |
| JP | H09-157405 | * | 6/1997 | ................ C08J 5/16 |

(Continued)

OTHER PUBLICATIONS

Gattiglia et al. Journal of Applied Polymer Science vol. 41 pp. 1411-1423 1990.*

(Continued)

*Primary Examiner* — Patrick Ryan
*Assistant Examiner* — Aaron Greso
(74) *Attorney, Agent, or Firm* — Bridget C. Sciamanna

(57) ABSTRACT

Included are nylon and polyurethane urea compositions such as in the form of powders, beads and flock to be included in extruded and molded articles containing a thermoplastic resin such as nylon 12. The addition of the powders, beads or flock improve flexibility and shape retention of such molded articles, for example in eyewear frames.

2 Claims, No Drawings

(56) References Cited

FOREIGN PATENT DOCUMENTS

| | | | | |
|---|---|---|---|---|
| JP | H09-221534 | * | 8/1997 | ............ C08G 18/10 |
| WO | WO 96/26915 | * | 9/1996 | ............ C07C 211/52 |
| WO | 0224776 | | 3/2002 | |

OTHER PUBLICATIONS

Ul Ides (Polyamide (nylon Plastic product information (c) 1986-2013, polyamide or nylon historical information taken as applicable to 1986 {http://plastics.ides.com/generics/22/polyamide-nylon}).*

Hansch and Leo, Chemical Reviews, (1971), pp. 526-616, 71.

Hansch and Quinlan and Lawrence, J. Organic Chemistry, 33, pp. 347-350 (1924).

T. Shibamoto, Capillary Gas Chromatography in Essential Oak Analysis, P Sandra and C. Bicchi (editors), Huethig (1987), pp. 259-274.

S. Siggia, "Quantitative Organic Analysis via Functional Group", 3rd Edition, Wiley & Sons, New York, pp. 559-561 (1963).

* cited by examiner

NON-TEXTILE POLYMER COMPOSITIONS AND METHODS

CROSS-REFERENCE TO RELATED APPLICATIONS

This application is a continuation of international application PCT/US2008/054942 filed Feb. 26, 2008, is a continuation-in-part of U.S. patent application Ser. No. 11/654,753, filed on Jan. 18, 2007, and this application claims the benefit of U.S. Application No. 60/865,091 filed on Nov. 9, 2006, claims the benefit of U.S. Application No. 60/837,011 filed on Aug. 11, 2006, and claims the benefit of U.S. Application No. 60/759,853 filed on Jan. 18, 2006, all of which are incorporated herein by reference.

BACKGROUND OF THE INVENTION

1. Field of the Invention

The present invention includes polymer compositions such as polyurethaneureas, polyamides and polyesters. The compositions may be in a variety of forms such as dispersions, powders, fibers, and beads. The compositions are useful in the preparation of many products including health and beauty products such as cosmetics, paint, household products such as fabric care compositions, apparel/footwear and textiles/furnishings.

2. Summary of Related Art

Polymers such as polyurethaneureas, polyamides, and polyesters have historically been used in preparing synthetic fibers. However, these polymers have other properties that may potentially offer benefits beyond the fiber form. Therefore, there is a need for polymer compositions and methods which emphasize these additional advantages.

One example of a suitable form for different polymers is a powder. Fine powders of synthetic polymers such as polyethylenes, polyamides, polyurethanes and polysiloxanes have been used in printing, coating and cosmetic applications. Although many particle size reduction techniques (such as solid state shear pulverization, cryogenic grinding, gas atomization, and high shear mixing and millings) are known in the art and have been applied in producing polymeric powders, the need exists for improved methods to produce fine, uniform particles especially for those elastomeric polymers such as segmented polyurethanes and polyurethaneureas.

There is a need for improved polymer compositions that may provide additional benefits not only for printing, coating, and cosmetic applications, but also for other applications such as painting and fabric care.

Fabric softeners are often used in addition to detergents to impart softness and/or fluffiness to washable fabrics. Fabric softeners also make fabrics feel smooth, decrease static cling, impart a pleasing fragrance, reduce drying time, reduce wrinkling and make ironing easier. However, the benefits of these properties generally decrease over time after washing.

The most common active components are based on long chain fatty type molecules called quaternary ammonium compounds, which are cationic in nature. Therefore, in order to prevent undesired reaction with detergents which may be anionic in nature, fabric softeners are generally introduced during fabric rinsing or drying.

In order to reduce the time and expense of fabric laundering, there is a need for fabric care compositions which may be added simultaneously with the detergent. There is also a need for fabric care compositions which extend the duration of the benefits of fragrance substantiation and ease of care associated with fabric softening compositions.

SUMMARY OF THE INVENTION

One embodiment provides a polyurethaneurea in the form of a powder or an aqueous dispersion. These powders or dispersions provide fabric care properties either alone or in combination with a detergent or fabric softener composition.

In one embodiment, a fabric care composition is in the form of a nonionic film-forming dispersion including a polyurethaneurea polymer and water. The polymer is the reaction product of a prepolymer with water as a chain extender where the prepolymer is the reaction product of a glycol or a mixture of glycols and 4,4'-methylenebis(phenyl isocyanate).

In another embodiment is a nonionic non-film-forming dispersion including water and a polyurethaneurea polymer. The polymer is the reaction product of a prepolymer and a chain extender including a diamine chain extender and water, where the polymer is the reaction product of a glycol (polyol) or a mixture of glycols and 4,4'-methylenebis(phenyl isocyanate). The polymer may then be filtered and ground or spray dried to provide a powder.

A further embodiment provides a method of extending perfume or fragrance substantiation on a fabric or garment. The method includes contacting the fabric or garment with a fragrance and a polyurethane urea composition in the form of a powder or an aqueous dispersion. The contact may occur in a variety of ways including, but not limited to, adding the fragrance and polyurethaneurea to a detergent or fabric softener prior to laundering and/or drying the fabric, adding them directly to the wash water, or introducing them during the rinsing cycle, either directly or in combination with a fabric softener composition.

A further embodiment provides a method of providing desired properties to a fabric or garment. The method includes contacting a fabric with a polyurethaneurea in the form of a powder or an aqueous dispersion. The desired properties which may be imparted to the fabric include, but are not limited to, shape retention, ease of care (i.e., ease of ironing), and anti-stain properties.

Also provided are segmented polyurethaneurea compositions in the form of fine powders. Methods to make such polyurethaneurea powders are also included. Additionally, in some embodiments are powders which provide water and/or oil absorbing properties.

Other polymer compositions and forms are provided. These compositions are useful for a variety of compositions including paints, cosmetics, and fabric care compositions, among others.

DETAILED DESCRIPTION OF THE INVENTION

As used herein, the term "powder" means a particulate material consisting of a loose aggregation of finely divided solid particles. For a fine powder the maximum dimension is smaller than 1 millimeter and the average particle size is less than 100 microns. However, larger particles sizes are also contemplated. For example a coarse powder may have particle sizes larger than 1 millimeter with an average particle size in the range from about 0.5 mm to about 2 mm.

As used herein, the term "film-forming" means that the material forms a continuous film in the absence of other reagents under the synthesis conditions disclosed herein.

As used herein, the term "non-film-forming" means that the material does not form a continuous film in the absence of other reagents under the synthesis conditions disclosed herein.

As used herein, the term "fabric" means any woven, nonwoven, knit, tuft, felt, braid, or bonded material assembled from fibers and/or yarns, including, but not limited to, those used in garments (clothing), sheets, towels, curtains, upholstery, and carpets.

As used herein, the term "fabric care composition" refers to any composition that may be applied to a fabric, especially during washing or drying of the fabric, to impart beneficial properties to the fabric. These properties include cleaning, removing oily and greasy marks, making fabrics feel smooth, decrease static cling, impart a pleasing fragrance, reduce drying time, reduce wrinkling and make ironing easier.

As used herein, the term "easy care" with respect to fabric means that the fabric will have fewer wrinkles after washing, may not require ironing or will have more ease of ironing.

Polyurethaneurea Compositions

The polyurethaneurea compositions of some embodiments may be in the form of an aqueous dispersion, powder, fiber, or bead. When a powdered form is desired, it may be isolated from the aqueous dispersion by filtering, drying and grinding or by spray drying of the dispersion. The solids content of the dispersion may vary. For example, solids content may be from about 5% to about 50%, more specifically from about 20% to about 40% by weight of the dispersion. Powders may have an average particle size of less than 100 microns, such as from about 50 to about 80 microns with no particle size greater than 1.0 mm, such as less than about 0.5 mm.

Another suitable method of preparing the polyurethaneurea powders of some embodiments is according to U.S. Pat. No. 6,475,412 to Roach, which is incorporated herein by reference. Roach discloses a method of extruding spandex under specific process conditions to provide a powder.

To prepare the anionic film-forming aqueous dispersion of some embodiments, a prepolymer is prepared which is a capped glycol. The prepolymer is the reaction product of:
- at least one hydroxyl-terminated polymer such as a polyether (including copolyethers), polycarbonate or polyester polyol component having a number average molecular weight of about 600 to about 3,500, for example, a poly(tetramethylene ether) glycol having a number average molecular weight of about 1,400 to about 2,400;
- a polyisocyanate, which is a mixture of 4,4'- and 2,4'-methylene bis(phenyl isocyanate) (MDI) isomers, with the ratio of the 4,4'-MDI to 2,4'-MDI isomers from about 65:35 to about 35:65; and
- at least one diol compound with: (i) hydroxy groups capable of reacting with the mixture of MDI isomers of the polyisocyanate and (ii) at least one carboxylic acid group capable of forming a salt upon neutralization, wherein the at least one carboxylic acid group is incapable of reacting with the mixture of MDI isomers of the polyisocyanate.

The prepolymer is then neutralized to form a salt, for example by inclusion of triethylamine and finally chain extended with a diamine chain extender and water to form the aqueous dispersion. Additives such as surfactants, anti-/defoamers, antioxidants, and thickening agents may be included.

The MDI isomer mixture for the anionic dispersion achieves a reduction in the prepolymer viscosity without the addition of a solvent. The MDI isomer mixture also serves to reduce the rate of the reaction. The prepolymer may be prepared either in a batch process or in a continuous process.

When included in some embodiments, the diol including hydroxy groups and a carboxylic acid group may be described as an acidic diol. Examples of useful acidic diols include 2,2-dimethylolacetic acid, 2,2-dimethylolpropionic acid (DMPA), 2,2-dimethylolbutanoic acid, 2,2-dimethylolpentanoic acid, and combinations thereof.

The nonionic film-forming dispersion of some embodiments includes a prepolymer, which is an isocyanate-terminated polyurethane prepolymer. This prepolymer is the reaction product of a hydroxyl-terminated polymer such as a polyol, such as poly(tetramethylene-co-ethylene ether) glycol or a mixture of poly(tetramethylene ether) glycol with ethoxylated polypropylene glycol and a diisocyanate such as 4,4'-methylenebis(phenyl isocyanate). This prepolymer is then chain extended with water and dispersed in water or dispersed in water followed by chain extension with water.

The nonionic non-film-forming dispersion of some embodiments includes a prepolymer, which is an isocyanate-terminated polyurethane prepolymer. This prepolymer is also the reaction product of a polyol such as a polybutadiene glycol or poly(tetramethylene ether) glycol and a diisocyanate such as 4,4'-methylenebis(phenyl isocyanate). This prepolymer may be chain extended with a combination of water and a diamine chain extender such as ethylene diamine or an amine-functional crosslinker such as polyvinylamine. Either a hydrophilic or hydrophobic glycol may be selected to produce a polymer powder having different water/oil absorbing capabilities. Also, the powder particle size can be adjusted by adjusting the viscosity of the prepolymer with the use of a solvent for dilution.

In some embodiments, a polyurethaneurea powder is made by high shear force dispersion of an isocyanate terminated prepolymer, with or without solvent, into a water medium containing a dispersant, and a chain extension reagent or a cross-linking agent. High shear force is defined as force sufficient to make particles no larger than 500 microns. The prepolymer can be made by reacting a polyol or a polyol copolymer or a polyol mixture, such as polyether glycols, polyester glycols, polycarbonate glycols, polybutadiene glycols or their hydrogenated derivatives, and hydroxy-terminated polydimethylsiloxanes, with a diisocyanate such as methylene bis(4-phenylisocyanate) (MDI) to form an NCO-terminated prepolymer or a "capped glycol". In a polymer composition, the molar ratio of NCO/OH is in the range of 1.2 to 5.0. An example of a chain extension reagent is an aliphatic diamine such as ethylene diamine (EDA). A chain cross-linking agent is an organic compound or a polymer with at least three primary amine or secondary amine functional groups capable of reacting with NCO groups. An organic solvent, soluble or insoluble in water, such as 1-methyl 2-pyrrolidinone (NMP) or xylenes can be used to dilute the prepolymer prior to the dispersion. The formed polyurethaneurea polymer fine particles dispersed in water can be used as such or isolated by filtration and drying into solid powders. Alternatively, a spray coating process which also provides a greater control of particle size may also be used.

The particle size of the powders of some embodiments may vary depending on the desired use. For example, the average particle size may be less than 1 millimeter (mm), also including an average particle size of less than 100 microns (μm).

In some embodiments, a segmented polyurethaneurea for making an elastomeric powder includes: a) a polyol or a polyol copolymer or a polyol mixture of number average molecular weight between 500 to 5000, including but not limited to polyether glycols, polyester glycols, polycarbonate glycols, polybutadiene glycols or their hydrogenated derivatives, and hydroxy-terminated polydimethylsiloxanes; b) a diisocyanate including aliphatic diisocyanates, aromatic diisocyanates and alicyclic diisocyanates; and c) an aliphatic diamine (i.e., a diamine chain extender) or its mixture with at least one diamine selected from the group consisting of an aliphatic diamine and an alicyclic diamine, each having 2 to 13 carbon atoms, or an amino-terminated polymer, or an organic compound or a polymer with at least three primary or secondary amine groups; and optionally a monoamine, primary or secondary, as a chain terminator.

Examples of polyether polyols that can be used in some embodiments include those glycols with two or more hydroxy groups, from ring-opening polymerization and/or copolymerization of ethylene oxide, propylene oxide, trimethylene oxide, tetrahydrofuran, and 3-methyltetrahydrofuran, or from condensation polymerization of a polyhydric alcohol, for example, a diol or diol mixtures, with less than 12 carbon atoms in each molecule, such as ethylene glycol, 1,3-propanediol, 1,4-butanediol, 1,5-pentanediol, 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. For example, a linear, bifunctional polyether polyol may be included, specifically, a poly(tetramethylene ether) glycol of molecular weight of about 1,700 to about 2,100, such as Terathane® 1800 (commercially available from INVISTA S.à r.l. of Wichita, Kans. and Wilmington, Del.) with a functionality of 2.

Examples of polyester polyols that can be used include those ester glycols with two or more hydroxy groups, produced by condensation polymerization of aliphatic polycarboxylic acids and polyols, or their mixtures, of low molecular weights with no more than 12 carbon atoms in each molecule. Examples of suitable polycarboxylic acids are malonic acid, succinic acid, glutaric acid, adipic acid, pimelic acid, suberic acid, azelaic acid, sebacic acid, undecanedicarboxylic acid and dodecanedicarboxylic acid. Example of suitable polyols for preparing the polyester polyols are ethylene glycol, 1,3-propanediol, 1,4-butanediol, 1,5-pentanediol 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. For example, a linear, bifunctional polyester polyol with a melting temperature of about 5° C. to about 50° C. may be included.

Examples of polycarbonate polyols that can be used include those carbonate glycols with two or more hydroxy groups, produced by condensation polymerization of phosgene, chloroformic acid ester, dialkyl carbonate or diallyl carbonate and aliphatic polyols, or their mixtures, of low molecular weights with no more than 12 carbon atoms in each molecule. Example of suitable polyols for preparing the polycarbonate polyols are diethylene glycol, 1,3-propanediol, 1,4-butanediol, 1,5-pentanediol, 1,6-hexanediol, neopentyl glycol, 3-methyl-1,5-pentanediol, 1,7-heptanediol, 1,8-octanediol, 1,9-nonanediol, 1,10-decanediol and 1,12-dodecanediol. For example, a linear, bifunctional polycarbonate polyol with a melting temperature of about 5° C. to about 50° C. may be included.

Examples of suitable diisocyanate components are 1,6-diisocyanatohexane, 1,12-diisocyanatododecane, isophorone diisocyanate, trimethyl-hexamethylenediisocyanates, 1,5-diisocyanato-2-methylpentane, diisocyanato-cyclohexanes, methylene-bis(4-cyclohexyl isocyanate), tetramethyl-xylenediisocyanates, bis(isocyanatomethyl)cyclohexanes, toluenediisocyanates, methylene bis(4-phenyl isocyanate), phenylenediisocyanates, xylenediisocyanates, and a mixture of such diisocyanates. For example the diisocyanate may be an aromatic diisocyanate such phenylenediisocyanate, tolylenediisocyanate (TDI), xylylenediisocyanate, biphenylenediisocyanate, naphthylenediisocyanate, diphenylmethanediisocyanate (MDI), and combinations thereof.

Examples of suitable diamine components (diamine chain extenders) are ethylenediamine, 1,2-propanediamine, 1,3-propanediamine, 2,2-dimethyl-1,3-propanediamine, 1,4-butanediamine, 1,5-pentanediamine, hexamethylene diamine, 1,7-heptanediamine, 1,8-octanediamine, 1,9-nonanediamine, 1,10-decanediamine, 1,12-dodecanediamine, 2-methyl-1,5-pentanediamine, cyclohexanediamines, cyclohexanebis(methylamine)s, isophorone diamine, xylylenediamines, and methylenebis(cyclohexylamine)s. A mixture of two or more diamines can also be used.

Examples of suitable amine-terminated polymers are bis (3-aminopropyl) terminated polydimethylsiloxane, amine terminated poly(acrylonitrile-co-butadiene), bis(3-aminopropyl) terminated poly(ethylene glycol), bis(2-aminopropyl) terminated poly(propylene glycol), and bis(3-aminopropyl) terminated polytetrahydrofuran.

Examples of suitable organic compounds or polymers with at least three primary or secondary amine groups are tris-2-aminoethyl amine, poly(amido amine) dendrimers, polyethylenimine, poly(vinylamine), and poly(allylamine).

Examples of the suitable monoamine component (d) include primary alkylamines such as ethylamine, butylamine, hexylamine, cyclohexylamine, ethanolamine and 2-amino-2-methyl-1-propanol, and secondary dialkylamines such as N,N-diethylamine, N-ethyl-N-propylamine, N,N-diisopropylamine, N-tert-butyl-N-methylamine, N-tert-butyl-N-benzylamine, N,N-dicyclohexylamine, N-ethyl-N-isopropylamine, N-tert-butyl-N-isopropylamine, N-isopropyl-N-cyclohexylamine, N-ethyl-N-cyclohexylamine, N,N-diethanolamine, and 2,2,6,6-tetramethylpiperidine.

In making a polyurethaneurea powder of some embodiments, a glycol is first reacted with a diisocyanate, optionally with a catalyst present, to form an NCO-terminated prepolymer or a "capped glycol". This reaction is typically carried out, in a molten form of uniformly blended mixture, with applied heat at temperatures of 45 to 98° C. for a period of 1 hour to 6 hours. The amounts of each reaction component, the weight of the glycol (Wgl) and the weight of the diisocyanate (Wdi), are regulated by the capping ratio (CR), which is defined as the mole ratio of the diisocyanate to the glycol as shown below:

$$CR=(Wdi/MWdi)/(Wgl/MWgl)$$

Where MWdi is the molecular weight of the diisocyanate and MWgl is the number average molecular weight of the glycol. According to the present invention, the capping ratio is in the range of 1.2 to 5.0, specifically between 1.5 and 3.0.

After the capping reaction is complete when all of the hydroxy (—OH) groups from the glycol molecules are consumed by the isocyanate (—NCO) groups from the diisocyanate to form a urethane bond, a viscous polyurethane prepolymer with terminal NCO groups is formed. This prepolymer is then added and dispersed into a water solution containing surface active reagents such as dispersants and anti-/defoamers and optionally chain-extending agents such as diamines. Alternatively, this prepolymer can be diluted with an organic solvent such as water-soluble N-methylpyrrolidone (NMP), N-ethyl pyrrolidone (NEP), dipropylene glycol dimethyl ether, or water-insoluble xylenes before dispersed in the water medium. The solid polymer particles are formed under the high shear force during the dispersion and upon the chain extension with water and/or diamine extenders. These polyurethaneurea particles can then be filtered and dried.

Additives such as antioxidants, pigments, colorants, fragrances, anti-microbial agents (like silver), active ingredients (moisturizers, UV-screens), surfactants, anti-/defoamers, solvents and the like can be blended into the polyurethaneurea particles before, during or after the dispersion of the prepolymer. In some cases it may be beneficial to put the additives in during the dispersion of the prepolymer to encapsulate the additive into the polyurethaneurea particles. Encapsulation of the additive may slow the diffusion of the additive out of the polymer matrix providing a delayed or time release of the additive. This delayed release is compared to the relatively faster release of an additive adsorbed on to the surface of a particle. Combinations of encapsulating and surface adsorbed additives may be included to provide quick release of one or more additives from the surface of a particle and a delayed release of the encapsulated additive.

Pigments may also be added to the polyurethaneurea compositions of some embodiments. Pigments may be added in a similar manner to other additives. Examples of pigments include carbon black and $TiO_2$. For a polyurethaneurea powder, the effect of pigments is shown in Table A below:

| Pigment Type | Powder color |
| --- | --- |
| base, no added pigment | white |
| ultramarine blue | light blue |
| ultramarine pink | light pink |
| black oxide | gray |
| orange oxide | light orange |
| yellow oxide | yellow |
| chromium green oxide | light green |

Additional examples of pigments are described hereinbelow.

Polyurethaneurea Beads

Some embodiments of the invention are polyureaurethane beads. One useful method for preparing such beads is disclosed in U.S. Pat. No. 5,094,914 to Figuly et al. ("Figuly"), which is incorporated herein by reference in its entirety. A segmented polyureaurethane composition, which may be any of those described herein, (such as those based on polyethers or polyesters) can be prepared. A solution including the polyureaurethane can be prepared with a solvent. A variety of useful solvents may be included such as amide solvents, including but not limited to dimethylacetamide (DMAc), dimethylformamide (DMF), and N-methylpyrrolidone (NMP). The polyureaurethane solution can then be introduced as droplets into a coagulating bath which solidifies the polymer in bead form. The coagulating bath can include a liquid that extracts the solvent of the polymer solution, but is not a solvent for the polymer, such as water.

Thus beads can be prepared having a diameter from about 1 mm to about 4 mm, having a void content of 60% to 90%, and having no visible pores on the surface at 5000× magnification.

Some embodiments of the present invention are polyureaurethane beads having a broader range of particle sizes, void content, and surface pores than previously disclosed.

The void content is based on the density of the beads:

Voids=[1−(bead density/bulk polymer density)]×100%

In some embodiments are polyureaurethane beads having a void content below 60%. These beads may be prepared by using a higher viscosity solution. For Example, solutions having Brookfield viscosities from about 1000 cps and above and solids content from about 12% and above produce beads that are denser, heavier, and smaller than beads made using the same bead making apparatus, but utilizing solutions having less than 1000 cps. In some embodiments are beads prepared from solutions that have high viscosities (>1000 cps) but have relatively low solids content (i.e. <10%). This can be accomplished by utilizing a polymer with a high average molecular weight, is branched, or a polymer that associates together in the solution through crystallization, hydrogen bonding, hard segment association, etc. For example, polyurethane urea based solutions will become more viscous with age.

Low viscosity solutions with relatively high solids content may be prepared through the use of polymers that shear thin, for example a liquid crystalline polymer or some spandex formulations or by using polymers that have low average molecular weight, or do not associate, hydrogen bond or crystallize in solution.

Another method of preparing smaller, more dense beads is to produce beads from solutions that produce void volumes of 60 to 90%, but in the coagulation and drying process to remove the solvent, some solvent is allowed to remain with the beads. The beads are then dried so that the residual solvent will redissolve and reprecipitate the polymer into a more dense structure.

Beads with void content above 90% may also be prepared. One method is to include polymers with low viscosities. However, as the viscosity is continuously lowered, within the same polymer formulation, a point is reached where the polymer is so dilute that it can not sustain the bead shape in the coagulation process and collapses (This process is disclosed in U.S. Pat. No. 5,126,181 for the preparation of flattened microporous disks). On the other hand, it is possible to choose or formulate polymers, in particular polyurethaneureas, which are stiffer in nature so that even when diluted still have enough stiffness to hold the bead shape without collapsing. In particular, it is possible within the family of polyurethaneureas, to synthesize or choose a formulation that is stiffer, but still has the highly desirable elastomeric nature (stretch and recovery) inherent. For example, a polyurethane urea that uses a polyether glycol of low average molecular weight, such as an average molecular weight of less than 1000 or less than 700, as the soft segment will be sufficient to produce a bead having a void content of greater than 90% that maintains a spherical shape.

In addition, other reactants or co-reactants could be used to modify the stiffness of the final polyureaurethane bead, e.g. different extenders than EDA (ethylene diamine) or coextenders with EDA, or isomers of MDI (4,4'-vs. 2,4-) and mixtures thereof. 1,4-phenylene diisocyanate or 1,4-phenylene diamine or a combination or mixture thereof will also produce stiffer polyureaurethanes than corresponding polyureaurethanes based on "traditional" MDI and EDA. It should also be appreciated that mixtures of polyureaurethanes having different stiffnesses could also be utilized to tailor or dial in the necessary stiffness required to attain void volumes greater than 90%. Other polymers or additives could be admixed into the solution to achieve the necessary stiffness and other requirements to make higher void volume beads.

In some embodiments are beads with controlled size pores on the surface. A micronized or nano-sized salt or other water-soluble material (e.g. polyethylene glycol) may be combined with the polyureaurethane solution prior to introduction to a coagulation bath. The water-soluble materials will leave a pore when the bead is coagulated and washed in water.

Also provided are methods for continuously or semi-continuously producing beads. In batch, stirred reactor process, solvent may build up in the water or polymer non-solvent. Excessive build up of solvent may lead to tackiness of the produced beads causing them to stick together or possibly even coalescing them. The buildup of solvent in the non-solvent (or water) may also slow down the coagulation of the beads due to insufficient thermodynamic incentive for the solvent to be "pulled" or diffuse into the non-solvent. The non-solvent is becoming more and more concentrated and nearly identical to the solvent as the solvent diffuses out of the beads or disks.

Even the semi-continuous process of some embodiments would allow for the production of about 500 grams of beads per 8-hour shift, a 10-fold increase over that of a batch, stirred reactor process. Beads can be "harvested" anytime after about 2-3 minutes after formation and moved to vessels other than that in which they were formed allowing for the continuous production of beads in the "process apparatus" for at least up to three 8 hour shifts.

In another embodiment, water in the "process apparatus" could be continuously flushed and the beads periodically or continuously harvested such that the beads could be produced continuously. A continuous or semi-continuous operation would be industrially favorable in comparison to a batch operation.

Harvesting or moving the beads from where they are formed to a different tank to be soaked and the residual DMAc solvent extracted can be accomplished by numerous methods. One method includes the use of a conveyer system including a conveyor belt. The belt could be a screen or include holes to allow water to pass through them, while retaining the beads thereon. Another method to transfer the beads away from the process apparatus is via a "waterfall." The waterfall method allows for the beads to be collected at one end of the tank away from where they are formed, by allowing some water and a significant number of the beads to spill over the edge of the forming tank into another tank. Since the beads float in the water/solvent mixture, this can be easily accomplished.

The polyurethaneurea beads of some embodiments have a wide range of applicability. This includes use in textiles, apparel and shoes, home furnishings, cosmetics and other household uses. As a bedding material, they may be included as an alternative to fiberfill such as in pillows. In shoes, beads may be included as a cushion for the shoe sole. Additionally, a combination of different size beads may be included in the same shoe sole to accommodate for varying pressure points within the sole, as well as in the inner soles, outer and upper shoe portions, particularly where beads are included in a "sandwich" construction in pleated or quilted constructions. The cushioning effect is also useful for furniture cushions and carpet padding. For example, the beads may be included in fibrous batting materials. Cushioning effects are also beneficial in headgear such as helmets or hats, straps for clothing, straps for luggage, and comfort grip applications such as those found on clubs, ski poles, hammers, bicycles, lawnmowers, steering wheels, etc.

The beads have a plethora of useful properties. For example, after having been compressed for 24 hours to a quarter of the original diameter, the beads regain 85% of their volume immediate and about 97% of their volume after 10 minutes. The sizes of the beads may vary. Beads may have a diameter of greater than 0.1 mm to 10 mm, such as from about 0.05 mm to about 8 mm. Individual beads have been prepared which have diameters of 0.5 mm, 0.8 mm, 1.0 mm, 2.5 mm, 3.0 mm, 4.0 mm, 5.0 mm, and 8.0 mm.

Individual beads may have a density in any suitable range, such as from about 0.05 g/cc to about 0.5 g/cc, including about 0.1 g/cc. Also, the beads have unique absorptions properties. For example, when placed in water, a bead of approximately 3 mm in diameter will absorb approximately 14% of its weight in water. However, when the bead is squeezed and then released in water, the bead will absorb up to about 350% its weight in water. These absorption properties demonstrate additional utility such as a delivery vehicle for substances such as fragrances, ointments, and other fluid compositions.

Polyamide Compositions

A variety of different polyamides may be used with some embodiments. Examples of suitable polyamides include Nylon 6, Nylon 12, and Nylon 6,6. The polyamide may be present in any desired form including fibers and powders. One suitable process for the preparation of polyamide powder is disclosed in U.S. Pat. No. 4,831,061 to Hilaire, which is incorporated herein by reference. Such powders are also commercially available under the trade name Orgasol® from ARKEMA. Of the commercially available powders, sizes range from about 5 microns to about 60 microns, including from about 5 to about 20 microns. Polyamide powders may also be provided in a broader range of sizes, such are having an average particle size in the range of about 50 microns to about 500 microns, including 100 microns. Coarser powders are also included such as those having an average particle size in the range of about 0.5 mm to about 5 mm, including about 1 mm.

Polyester Compositions

A variety of different polyesters are also useful for inclusion in some embodiments. Examples include polyalkylene terephthalate, polyalkylene naphthalate and polyalkylene isophthalate. Examples of polyalkylene terephthalates are fiber-forming linear condensation polymers having carboxyl linking radicals in the polymer chain such as polyethylene terephthalate ("2GT" or "PET"), polytrimethylene terephthalate ("3GT" or "PTT"), and polytetramethylene terephthalate ("4GT").

The polyester composition may be in any desired form including fibers, flock, and powders.

In the absence of an indication to the contrary, a reference to "polyalkylene terephthalate" is meant to encompass copolyesters, i.e., polyesters made using 3 or more reactants, each having two ester forming groups. For example, a copoly (ethylene terephthalate) can be used in which the comonomer used to make the copolyester is selected from the group consisting of linear, cyclic, and branched aliphatic dicarboxylic acids having 4 to 12 carbon atoms (for example butanedioic acid, pentanedioic acid, hexanedioic acid, dodecanedioic acid, and 1,4-cyclo-hexanedicarboxylic acid); aromatic dicarboxylic acids other than terephthalic acid and having 8 to 12 carbon atoms (for example isophthalic acid and 2,6-naphthalenedicarboxylic acid); linear, cyclic, and branched aliphatic diols having 3 to 8 carbon atoms (for example 1,3-propanediol, 1,2-propanediol, 1,4-butanediol, 3-methyl-1,5-pentanediol, 2,2-dimethyl-1,3-propanediol, 2-methyl-1,3-propanediol, and 1,4-cyclohexanediol); and aliphatic and aromatic ether glycols having 4 to 10 carbon atoms (for example, hydroquinone bis(2-hydroxyethyl) ether, or a poly(ethylene ether) glycol having a molecular weight below about 460 daltons, including diethyleneether glycol). The comonomer typically can be present in the copolyester at a level in the range of about 0.5 to about 15 mole %.

Flock

In some embodiments are the polymer compositions in the form of flock. Flock is a very short precision cut or pulverized fiber used to produce a velvet like coating on cloth, rubber, film, or paper. Flock may be used as filler in plastic, paper, rubber, or similar compositions to increase impact strength, improve moldability, or add a decorative appearance to the finished product. Flock may be a fiber, generally between the length of about 0.040 inches to about 0.250 inches (0.1 mm to 6.25 mm). The diameter is generally between about 10 to about 100 microns. Flock of different colors may be prepared from a variety of different synthetic and natural fibers such as polyamides, polyesters, cotton, and rayon.

Dye Information

A variety of different dyes, colorants and pigments may be used to add color to the compositions of some embodiments. For example, certain dyes are most useful for adding color to the polyamide and polyester compositions while pigments may be added to the polyureaurethane compositions.

Among the colorants used for some embodiments, including cosmetic compositions are inorganic colorants and organic colorants which include synthetic and natural colorants. Inorganic colorants include TiO2, iron oxides and ultramarines. Synthetic organic colorants include lakes, toners and pigments, such as those described in U.S. Pat. No. 4,909,853, herein incorporated by reference. An example of a natural organic colorant is carmine.

One suitable method for preparing a colored nylon powder includes dyeing in a dye beaker heated on a hot plate with a magnetic stirrer. This ensures that powders are well agitated by the stirrers to prevent formation of lumps and ensuring even dye uptake throughout the batch:

1. Set dye bath to pH6.0 with phosphate buffers
2. Add 1% (on weight) of Levegal SER (Anionic levelling agent)
3. Add pre-dissolved dyestuff
4. Add nylon powder
5. Raise to boil at 2° C./min rate of rise. Hold at temperature for 30 minutes.
6. Add 1 g/l Sandacid GBV (acid donor-slowly releases acid into dyebath to drop pH to pH 5.0-5.5)
7. Hold at temperature for 30 minutes.
8. Cool.
9. Pour dye-bath and powder through a fine filter and rinse.
10. Collect powder and dry in a heated cabinet.

For nylon of any form including fiber, flock, and powder, the most commonly used dyestuffs are non-metallized and metallized acid dyes. Both of these give a good shade range and a certain degree of colour fastness to both washing and UV. The metallized dyes will give the best fastness to UV and washing, but the shade range is limited to the more muted shades. Bright shades are only achieved either with the non-metallized acid dyes, which do not perform so well under UV and washing, or there is a limited range of special reactive acid dyes available which offer the best performance to washing, but which have similar fastness performance to UV as the non-metallized acid dyes. These reactive dyes tend to be more expensive and the shade depth is limited depending upon the available amine ends in the nylon powder/flock.

For polyester of any form including fiber, flock, and powder, disperse dyes are the only dyes that can dye standard disperse dyeable polyester. However, if you have cationic dyeable polyester, then either basic (cationic) or disperse dyes can be used All of these types of dye classes can be obtained from the major suppliers such as Huntsman (formerly Ciba Textile Effects) and DyStar. See table below for list of commercially available dyes by supplier and class.

| Supplier | Acid non-metallized | Acid metallized | Reactive acid | Disperse | Cationic |
|---|---|---|---|---|---|
| Huntsman | Tectilon, Erionyl | Lanaset | Eriofast, Lanasol, Lanaset | Terasil | Maxilon |
| DyStar | Telon | Isolan | Stanalan | Dianix | Astazone |

Fragrances

There is a range of fragrance materials that deposit well on, or are retained well on, spandex (i.e., segmented polyureaurethane). Such materials include, but are not limited to, the following two categories, Category A and Category B as set forth below.

Category A: hydroxylic materials which are alcohols, phenols or salicylates, with an octanol/water partition coefficient (P) whose common logarithm ($\log_{10}$ P) is 2.5 or greater, and a gas chromatographic Kovats index (as determined on polydimethylsiloxane as non-polar stationary phase) of at least 1050.

The octanol-water partition coefficient (or its common-logarithm "logP") is well-known in the literature as an indicator of hydrophobicity and water solubility (see Hansch and Leo, Chemical Reviews, 71, 526-616, (1971); Hansch, Quinlan and Lawrence, J. Organic Chemistry, 33, 347-350 (1968). Where such values are not available in the literature they may be measured directly, or estimated approximately using mathematical algorithms. Software providing such estimations is available commercially, for example "LogP" from Advanced Chemistry Design Inc.

Materials having $\log_{10}$ P of 2.5 or more are somewhat hydrophobic.

Kovats indices are calculated from the retention time in a gas chromatographic measurement referenced to the retention time for alkanes [see Kovats, Helv.Chim.Acta 41, 1915 (1958)]. Indices based on the use of a non-polar stationary phase have been used in the perfumery industry for some years as a descriptor relating to the molecular size and boiling point of ingredients. A review of Kovats indices in the perfume industry is given by T Shibamoto in "Capillary Gas Chromatography in Essential Oil Analysis", P Sandra and C Bicchi (editors), Huethig (1987), pages 259-274. A common non-polar phase which is suitable is 100% dimethyl polysiloxane, as supplied for example under a variety of tradenames such as RP-1 (Hewlett-Packard), CP Sil 5 CB (Chrompack), OV-1 (Ohio Valley) and Rtx-1 (Restek).

Materials of low Kovats index tend to be volatile and are not retained well on many fibers.

Category A includes alcohols of general formula ROH where the hydroxyl group may be primary, secondary or tertiary, and the R group is an alkyl or alkenyl group, optionally branched or substituted, cyclic or acyclic, such that ROH has partition coefficient and Kovats properties as defined above. Alcohols of Kovats index 1050 to 1600 are typically monofunctional alkyl or arylalkyl alcohols with molecular weight falling within the range 150 to 230.

Category A also includes phenols of general formula ArOH, where the Ar group denotes a benzene ring which may be substituted with one or more alkyl or alkenyl groups, or with an ester grouping —$CO_2A$, where A is a hydrocarbon radical, in which case the compound is a salicylate. ArOH has partition coefficient and Kovats index as defined above. Typically, such phenols with Kovats index 1050 to 1600 are monohydroxylic phenols with molecular weight falling within the range 150 to 210.

Examples of fragrance materials in category A are 1-(2'-tert-butylcyclohexyloxy)-butan-2-ol, 3-methyl-5-(2',2',3'-trimethylcyclopent-3-enyl)-pentan-2-ol, 4-methyl-3-decen-5-ol, amyl salicylate, 2-ethyl-4(2',2',3-trimethylcyclopent-3'-enyl)but-2-enol, borneol, carvacrol, citronellol, 9-decenol, dihydroeugenol, dihydrolinalol, dihydromyrcenol, dihydroterpineol, eugenol, geraniol, hydroxycitronellal, isoamyl salicylate, isobutyl salicylate, isoeugenol, linalool, menthol, nerolidol, nerol, para tert-butyl cyclohexanol, phenoxanol, terpineol, tetrahydrogeraniol, tetrahydrolinalol, tetrahydromyrcenol, thymol, 2-methoxy-4-methylphenol, (4-isopropylcyclohexyl)-methanol, benzyl salicylate cyclohexyl salicylate, hexyl salicylate, patchouli alcohol, and farnesol.

Category B esters, ethers, nitriles, ketones or aldehydes, with an octanol/water partition coefficient (P) whose common logarithm ($\log_{10} P$) is 2.5 or greater, and a gas chromatographic Kovats index (as determined on polydimethylsiloxane as non-polar stationary phase) of at least 1300.

Fragrances of Category B are of general formula Rx, where X may be in a primary, secondary or tertiary position, and is one of the following groups: —$CO_2A$, —COA, —OA, —CN or —CHO. The groups R and A are hydrocarbon residues, cyclic or non-cyclic and optionally substituted. Typically, the materials of Category B with Kovats index not exceeding 1600 are monofunctional compounds with molecular weights in the range 160 to 230.

Examples of fragrance materials in category B are 1-methyl-4-(4-methyl-3-pentenyl)-3-cyclohexene-1-carbaldehyde, 1-(5',5'-dimethylcyclohexenyl)-pent-en-1-one, 2-heptyl cyclopentanone, 2-methyl-3-(4'-tert-butylphenyl) propanal, 2-methylundecanal, 2-undecenal, 2,2-dimethyl-3-(4'-ethylphenyl)-propanal, 3-(4'-isopropylphenyl)-2-methylpropanal, 4-methyl-4-phenylpent-2-yl acetate, allyl cyclohexyl propionate, allyl cyclohexyloxyacetate, amyl benzoate, methyl ethyl ketone trimers, benzophenone, 3-(4'-tert-butylphenyl)-propanal, caryophyllene, cis-jasmone, citral diethyl acetal, citronellal diethyl acetal, citronellyl acetate, phenylethyl butyl ether, alpha-damascone, beta-damascone, delta-damascone, gamma-decalactone, dihydro isojasmonate, dihydrojasmone, dihydroterpinyl acetate, dimethyl anthranilate, diphenyl oxide, diphenylmethane, dodecanal, dodecen-2-al, dodecane nitrile, 1-ethoxy-1-phenoxyethane, 3-(1'-ethoxyethoxy)-3,7-dimethylocta-1,6-diene, 4-(4'-methylpent-3'-enyl)-cyclohex-3-enal, ethyl tricyclo[5.2.1.0-2,6-]decane-2-carboxylate, 1-(7-isopropyl-5-methylbicyclo[2.2.2]oct-5-en-2-yl)-1-ethanone, allyl tricyclodecenyl ether, tricyclodecenyl propanoate, gamma-undecalactone, n-methyl-n-phenyl-2-methylbutanamide, tricyclodecenyl isobutyrate, geranyl acetate, hexyl benzoate, ionone alpha, ionone beta, isobutyl cinnamate, isobutyl quinoline, isoeugenyl acetate, 2,2,7,7-tetramethyltricyloudecan-5-one, tricyclodecenyl acetate, 2-hexylcyclopentanone, 4-acetoxy-3-pentyltetrahydropyran, ethyl 2-hexylacetoacetate, 8-isopropyl-6-methylbicyclo [2.2.2]oct-5-ene-2-carbaldehyde, methyl 4-isopropyl-1-methylbicyclo[2.2.2]oct-5-ene-2-carboxylate, methyl cinnamate, alpha iso methyl ionone, methyl naphthyl ketone, nerolin, nonalactone gamma, nopyl acetate, para tert-butyl cyclohexyl acetate, 4-isopropyl-1-methyl-2-[1'-propenyl]-benzene, phenoxyethyl isobutyrate, phenylethyl isoamyl ether, phenylethyl isobutyrate, tricyclodecenyl pivalate, phenylethyl pivalate, phenylacetaldehyde hexylene glycol acetal, 2,4-dimethyl-4-phenyltetrahydrofuran, rose acetone, terpinyl acetate, 4-isopropyl-1-methyl-2-[1'-propenyl]-benzene, yara, (4-isopropylcyclohexadienyl)ethyl formate, amyl cinnamate, amyl cinnamic aldehyde, amyl cinnamic aldehyde dimethyl acetal, cinnamyl cinnamate, 1,2,3,5,6,7,8,8a-octathyro-1,2,8,8-tetramethyl-2-acetyl naphthalene, cyclo-1,13-ethylenedioxytridecan-1,13-dione, cyclopentadecanolide, hexyl cinnamic aldehyde, 1,3,4,6,7,8-hexahydro-4,6,6,7,8,8-hexamethylcyclopenta[g]-2-benzopyran, geranyl phenyl acetate, 6-acetyl-1-isopropyl-2,3,3,5-tetramethylindane, and 1,1,2,4,4,7-hexamethyl-6-acetyl-1,2,3,4-tetrahydronaphthalene.

While this is an extensive list of fragrances and perfumes that work especially well with spandex compositions, it is recognized that a variety of other fragrances are also useful in some embodiments. Fragrances may include a substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances.

A non-limiting examples of fragrances include: hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma, orange oil; lemon oil; grapefruit oil; bergamot oil; clove oil; dodecalactone gamma; methyl-2-(2-pentyl-3-oxo-cyclopentyl) acetate; beta-naphthol methylether; methyl-beta-naphthylketone; coumarin; decylaldehyde; benzaldehyde; 4-tert-butylcyclohexyl acetate; alpha,alpha-dimethylphenethyl acetate; methylphenylcarbinyl acetate; cyclic ethyleneglycol diester of tridecandioic acid; 3,7-dimethyl-2,6-octadiene-1-nitrile; ionone gamma methyl; ionone alpha; ionone beta; petitgrain; methyl cedrylone; 7-acetyl-1,2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8,8-hexamethylcyclopenta-gamma-2-benzopyran-e; ambroxane; dodecahydro-3a,6,6,9a-tetramethylnaphtho-[2,1b]furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; hydroxycitronellal and indol; phenyl acetaldehyde and indol; geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate, and combinations thereof.

Fabric Care Compositions

The polyurethaneurea compositions prepared by the methods described above deliver surprisingly improved shape retention properties to fabrics. Furthermore, they also provide ease of care or easy care properties to fabrics. In other words, fabrics treated with the polyurethaneurea compositions have fewer wrinkles after washing and are easier to iron.

The polyurethaneurea compositions of some embodiments also have surprisingly good water and oil absorption, especially when applied to a fabric. This is particularly important for anti-stain properties. After a fabric has been contacted with a polyurethaneurea composition of some embodiments, the polyurethaneurea will absorb moisture and oil from stain-causing sources and thereby limit the absorption of the fabric itself.

Due to the absorption properties, the polyurethaneurea compositions also assist in prolonging fragrance substantiation in a fabric which has been contacted by the composition. This results from the absorption and subsequent gradual release of the fragrance by the polyurethaneurea composition.

The fabric care composition of some embodiments may include a fabric softener or detergent to which the polyurethaneurea compositions may be added. These polyurethaneurea compositions may also be in any form such as a dispersion or powder. Alternatively, the polyurethaneurea composition may be added directly to the fabric, to a washing machine, wash water (for hand washing), or to an automatic dryer.

Furthermore, the powder or dispersion may be used as a replacement of fabric softener to deliver anti stain properties to garments via home laundering. Fabric softeners are frequently used to deliver perfume or fragrance to fabrics and secondarily to deliver fabric softness. The fabric softening aspect is not necessarily needed when tumble drying is used since fabrics which are tumble dried are already very soft.

The detergent compositions of some embodiments normally contains an anionic, nonionic, amphoteric or ampholytic surfactant or a mixture thereof, and frequently contains, in addition, an organic or inorganic builder.

Fabric softeners will generally include an active component such as a quaternary ammonium salt. Examples of non-cyclic quaternary ammonium salts include tallow trimethyl ammonium chloride; ditallow dimethyl ammonium chloride; ditallow dimethyl ammonium methyl sulfate; dihexadecyl dimethyl ammonium chloride; di(hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium methyl sulfate; dihexadecyl diethyl ammonium chloride; dihexadecyl dimethyl ammonium acetate; ditallow dipropyl ammonium phosphate; ditallow dimethyl ammonium nitrate; and di(coconut-alkyl) dimethyl ammonium chloride.

Other optional components of the fabric care compositions of some embodiments conventional in nature, and generally are present from about 0.1% to about 10% by weight of the composition. Such optional components include, but are not limited to, colorants, perfumes, bacterial inhibitors, optical brighteners, opacifiers, viscosity modifiers, fabric conditioning agents in solid form such as clay, fabric absorbency boosters, emulsifiers, stabilizers, shrinkage controllers, spotting agents, germicides, fungicides, anti-corrosion agents, anti-strain polymers, etc.

The fabric care compositions of some embodiments can be prepared by conventional methods. Homogenizing is not necessary. A convenient and satisfactory method is to prepare a premix of softeners in water at about 150° F. which is then added to a hot aqueous solution of the other components. Temperature-sensitive components can be added after the fabric conditioning composition is cooled to about room temperature.

The fabric care compositions of some embodiments may be used by adding to the rinse cycle of conventional home laundry operations. Alternatively, the fabric care compositions may be added to a detergent prior to the wash cycle, directly to the fabric, or with hand washing, either as part of a detergent or fabric softening composition or directly to the wash water.

The fabric care compositions may be applied in any form known in the art such as a powder, a liquid, a solid tablet, an encapsulate liquid (for example a composition encapsulated with polyvinylalcohol), or in the case of application for an automatic dryer, in a non-woven sheet.

The fabric care compositions of some embodiments may be added in any amount necessary to achieve the desired properties of the fabric. For example, the fabric care compositions may be added in an amount from about 0.05% to about 1.5%, for example, from about 0.2% to about 1%, by weight of the aqueous rinsing bath or wash water.

When present as an aqueous dispersion, the polyurethaneurea compositions of some embodiments may be present in the fabric care composition from about 0.1% to about 20% by weight of the fabric care composition, for example from about 5% to about 15%. When present as a powder, the polyurethaneurea compositions may be present in the fabric care composition from about 0.1% to about 20% by weight of the fabric care composition, for example from about 0.5% to about 10%, or from about 1% to about 5%.

Alternatively, the polyurethaneurea powder or dispersion may be added as a replacement for the fabric care composition instead of as a component of the fabric care composition, where the polyurethaneurea composition may be added as 100%. In this instance, the polyurethaneurea composition may be added directly to the wash water or rinsing water in amount from about 0.05% to about 1.5%, specifically, from about 0.2% to about 1%, by weight of the rinsing water or wash water.

Cosmetic Compositions

Nylon (polyamide) and polyurethaneurea powders have many properties that make that useful for inclusion with cosmetic compositions. Among these properties are oil, water, and sweat absorbency. These properties are especially useful for applications such as sweat absorbency for deodorants or anti-perspirants when in contact with skin. These properties are also useful for sebum control for skin contact products, for skin care, and in decorative cosmetics.

In one embodiment are polymer powders having antimicrobial activity to reduce bacterial growth and malodor. With the addition of an odor absorber, such as zinc oxide, the powder may have increased odor prevention.

The powders of some embodiments have surprisingly good water and oil absorption. In one embodiment, polyurethaneurea powders are formed, by the method described above, which have a specific particle size and are suitable for application as water or sweat absorbers in deodorant and anti-perspirant compositions or oil (sebum) absorbers in skin care or make-up compositions. Additional embodiments include powders with antimicrobial additives for enhanced odor protection, powders with additive fragrances for pleasant aromas, and powders for cosmetic and body care end uses. Non-limiting examples of cosmetic compositions to which the powders, beads, fibers, and dispersions of some embodiments include deodorants such as spray, stick, or roll-on anti-perspirants; make-up and color cosmetics such as powder (blush/bronzer/highlighter), foundation, eye shadow, eye liner, mascara, lipstick/lip gloss, and nail polish; skin care compositions such as body and facial moisturizers, shaving and after shave gels and creams, bar soap, and body wash/cleanser; hair care such as shampoos, conditioners, and styling products; and oral care including toothpastes.

The polyamide and polyurethaneurea powders of some embodiments have great feel and touch properties. For example, they have good gliding with silky and smooth touch.

The polyurethaneurea powders of the invention show very high water and sweat absorption by mass properties and at the same time show good oil absorption values. Very high water absorption is defined to be values greater than three times higher versus NY-6 powder (from Arkema commercially available from Lehmann and Voss & Co. of Hamburg, Germany). Good oil absorption values are defined as comparable to nylon 12 (Arkema) and higher than polymethyl methacrylate, polyethylene and polyurethane from KOBO (Kobo Products of South Plainfield, N.J. and St. Agne France). The polyurethaneurea powders of the invention show that the water or sweat absorption is extremely fast (immediate). Fast water absorption is defined to be 100 times faster than talc.

The fast and high mass of water absorption by the polyurethaneurea powders described herein combined with their compressibility also provide benefits for anti-aging and anti-wrinkle products. The powders may be used as fillers for skin wrinkles in anti-aging skin care compositions. The powders are hydrophilic, compressible micro-spheres with volumizing effects to stretch out the skin reducing or eliminating the appearance of wrinkles.

For applications of powders in cosmetics and body care applications, particles smaller than 100 micron are suitable to feel smooth on the skin and be unnoticed by the wearer. Ideally average particle size should be less than 50 microns. In one embodiment, powders of polyurethaneurea were included 90% of particles smaller than 42 microns, which may be achieved by filtering or by controlling parameters of a spray drying process.

In another embodiment are polyurethaneurea beads or powders as exfoliating agents in cleanser, scrubs, shower gels, etc. Typically materials such as ground nuts including apricot kernel have been included as exfoliating/scrubbing/peeling agents in cosmetic compositions. However, these tend to be hard and have very sharp edges which result in an unpleasant feeling. By contrast, the polyurethaneurea beads and powders of some embodiments may have a very spherical shapes, rounded surfaces, and a silky feel making them more "skin-friendly," while maintaining the effect of a hard material. The powders or beads may be added to a cleanser composition in any amount to achieve the desired effect. Particle sizes may also vary, generally greater than about 100 microns in order to be noticed by the consumer.

In another embodiment are polyurethaneurea dispersions which are film-forming for curl retention or anti-frizz properties in hair care compositions (gel, spray, shampoo, conditioner, etc.) Colored or pigmented polyurethaneurea powders can be used for non-permanent coloration of the hair.

The polymer compositions may be included in any composition up to 100% by weight of the composition. Suitable ranges of nylon, polyester, and polyurethaneurea inclusion in compositions based on the weight of the composition include 1-20% by weight, 1-15% by weight 5-10% by weight, and 25-75% by weight. The amount used depends on the application and the desired effect.

Paint Compositions

In some embodiments are paint compositions including polyurethaneurea, polyester and polyamide compositions. The paint may be any of those known in the art including latex, acrylic and oil based paint including primers, sealers, and coatings. The polyurethaneurea, polyester and polyamide compositions may be added to paint in any form to achieve a desired effect.

The addition of the polymer in the powder, short fiber, or bead form, may be included to provide texture to the paint composition. Also, if the powders, fibers or bead have been dyed or colored, the will also achieve a different paint effect. Such effects are extremely desirable given the recent interest in alternate painting techniques and faux finishes. The compositions of the some embodiments provide alternative surface characteristics such as texture and color without additional painting steps. Furthermore, a dual color effect or multiple color effect may be achieved, by adding color to the base paint and one or more separate colors in the powder/beads/fibers.

In addition to the visible effects of color and texture, the addition of flock to paint compositions has additional benefits. Paint compositions that include these flock fibers provide better coverage of uneven areas of walls/surfaces, higher flexibility, and resistance to cracking. Furthermore, they provide a wall paper effect through a paint application.

In addition to the visible effects of color and texture, the addition of polyurethaneurea dispersion to paint compositions has additional benefits. Paint compositions that include these dispersions may provide better coverage, especially on uneven surfaces, and resistance to cracking. This is demonstrated by the examples.

Alternatively, the addition of the polymer in the powder, short fiber, or bead form may be included to provide anti-skid properties to the paint compositions. This is accomplished by increasing the friction painted surface, in comparison to a traditional paint composition.

Thermoplastic Composition

The powders, beads, and flock of several embodiments herein are also useful as additives to a thermoplastic polymer composition for reinforcement and other beneficial properties such as improved bending/flexibility and improved shape retention. The thermoplastic may be any suitable polymer including nylon (polyamide), polyethylene, polypropylene, polystyrene, polyester, polycarbonate, polyvinyl chloride (PVC), polymethacrylate, and combinations thereof. The powders, beads or flock may be chosen from any of the nylon and polyurethaneurea compositions described herein.

The molded and shaped thermoplastic polymer compositions may be prepared by adding the powder, beads or flock to a commercially available thermoplastic polymer composition, such as in the form of pellets. This combination is then extruded and formed such as in the form of a sheet.

One example of a molded article is eyeglass frames. To prepare such an article, any suitable polymer such as nylon 12 polymer or polycarbonate may be used. The polymer pellets may be combined with powders of polyurethaneurea or nylon to improve shock resistance, flexibility, and shape retention. However, the powders, beads or flock as described herein also may provide other aesthetic properties due to the combination of different polymer materials, especially where the powder bead or flock particles remain as particles within the extruded/molded article. These aesthetic properties may be emphasized when the composition includes polymers, beads, powders or flock including different dyes and pigments.

The features and advantages of the present invention are more fully shown by the following examples which are provided for purposes of illustration, and are not to be construed as limiting the invention in any way.

EXAMPLES

Example

Capped glycol prepolymer, formed from Terathane® E2538 glycol (Supplied by INVISTA, S.à r.l.) and Isonate® 125MDR and with a capping ratio of 1.696, was obtained from a developmental LYCRA® spandex production line. LYCRA® is INVISTA's registered trademark for spandex. This prepolymer of 300 grams was mixed with 150 grams of NMP solvent in a plastic bottle for 10 minutes to reduce the viscosity. The diluted mixture was poured into a steel tube to be injected into a stainless steel container for dispersing. The container had 2000 grams of de-ionized water, 30 grams of T DET N14 surfactant (commercially available from Harcros of Kansas City, Kans.) and 4.5 grams of ethylenediamine chain extender which were premixed and cooled to 5° C. The diluted prepolymer was injected under air pressure at about 40 psi through a tubing of ⅛ inch inner diameter, a high-speed laboratory disperser (model number, HSM-100LC commercially available from Charles Ross & Son Company of Hauppauge, N.Y.) was operated at 5000 rpm. The addition of diluted prepolymer was completed within 15 minutes, the formed milky dispersion was continued to disperse for additional 5 minutes. Back weighing of the container gave the total amount of diluted capped glycol added into the dispersion being 328 grams, equivalent to 218.7 grams of capped glycol prepolymer added into the dispersion. Additive 65 foam controlling agent of 3 grams (commercially from Dow Corning of Midland, Mich.) was added to the dispersion, and the dispersion was allowed for mixing at 5000 rpm for another 30 minutes before pouring into a plastic bottle.

The average particle size of the dispersion was determined to be 52.83 micron, with 95% of the particles below 202.6 microns, by the use of a Microtrac X100 particle size analyzer (Leeds, Northrup).

Example 2

The same ingredients and dispersion procedures were used as in Example 1, except that 4.5 grams ethylenediamine chain extender was added after the diluted prepolymer was dispersed into water mixture. Back weighing of the container gave the total amount of diluted capped glycol added into the dispersion being 329 grams, equivalent to 219 grams of capped glycol prepolymer added into the dispersion. The average particle size of the dispersion was determined to be 33.45 micron, with 95% of the particles below 64.91 microns. The solid polymer particles do not form into films when isolated.

Example 3

Capped glycol prepolymer was prepared by reacting 500 grams of Krasol® HLB 2000 glycol (Supplied by Sartomer Company, Inc. at Exton, Pa.) and 105.86 grams of Isonate®125MDR at 90° C. for 120 minutes in a 2000 ml reaction kettles equipped with a heating mantle and a mechanical agitator. The reaction was carried out in a nitrogen filled dry box. After the reaction, the prepolymer had a NCO group wt % of 2.98 as determined by titration method. This prepolymer was poured into a steel tube to be injected into a stainless steel container for dispersing. De-ionized water (2000 grams) was mixed at room temperature in the container with 30 grams of T DET N14 surfactant (commercially available from Harcros of Kansas City, Kans.) and 3 grams of Additive 65 foam controlling agent (commercially from Dow Corning of Midland, Mich.). The prepolymer was injected under air pressure at about 80 psi through a tubing of ⅛ inch inner diameter, a high-speed laboratory disperser (model number, HSM-100LC commercially available from Charles Ross & Son Company of Hauppauge, N.Y.) was operated at 5000 rpm. The addition of diluted prepolymer was completed within 15 minutes, the formed milky dispersion was continued to disperse for additional 5 minutes. Back weighing of the container gave the total amount of diluted capped glycol added into the dispersion being 422 grams. Ethylenediamine chain extender of 4.5 grams was added to the dispersion and the dispersion was allowed for mixing at 5000 rpm for another 30 minutes. The average particle size of the formed dispersion was determined to be 49.81 micron, with 95% of the particles below 309.7 microns.

Example 4

The procedures were the same as in Example 3, except that a mixture of glycols with 250 grams of Terathane® 1800 glycol and 250 grams of Krasol® HLB 2000 glycol was used to form the prepolymer. A total of 465 grams of prepolymer was dispersed. The average particle size of the formed dispersion was determined to be 13.67 micron, with 95% of the particles below 38.26 microns.

Example 5

The preparation of the prepolymers was conducted in a glove box with nitrogen atmosphere. A 2000 ml Pyrex® glass reaction kettle, which was equipped with an air pressure driven stirrer, a heating mantle, and a thermocouple temperature measurement, was charged with about 382.5 grams of Terathane® 1800 glycol (commercially available from INVISTA, S.à r.l., of Wichita, Kans. and Wilmington, Del.) and about 12.5 grams of 2,2-dimethylopropionic acid (DMPA). This mixture was heated to about 50° C. with stirring, followed by the addition of about 105 grams of Lupranate® MI diisocyanate (commercially available from BASF, Wyandotte, Mich.). The reaction mixture was then heated to about 90° C. with continuous stirring and held at about 90° C. for about 120 minutes, after which time the reaction was completed, as the % NCO of the mixture declined to a stable value, matching the calculated value (% NCO aim of 1.914) of the prepolymer with isocyanate end groups. The viscosity of the prepolymer was determined in accordance with the general method of ASTM D1343-69 using a Model DV-8 Falling Ball Viscometer, (sold by Duratech Corp., Waynesboro, Va.), operated at about 40° C. The total isocyanate moiety content, in terms of the weight percent of NCO groups, of the capped glycol prepolymer was measured by the method of S. Siggia, "Quantitative Organic Analysis via Functional Group", 3rd Edition, Wiley & Sons, New York, pp. 559-561 (1963), the entire disclosure of which is incorporated herein by reference.

Example 6

A solvent-free prepolymer, as prepared according to the procedures and composition described in Example 5, was used to make the polyurethaneurea aqueous dispersion of the present invention.

A 2,000 ml stainless steel beaker was charged with about 700 grams of de-ionized water, about 15 grams of sodium dodecylbenzenesulfonate (SDBS), and about 10 grams of triethylamine (TEA). This mixture was then cooled with ice/water to about 5° C. and mixed with a high shear laboratory mixer with rotor/stator mix head (Ross, Model 100LC) at about 5,000 rpm for about 30 seconds. The viscous prepolymer, prepared in the manner as Example 1 and contained in a metal tubular cylinder, was added to the bottom of the mix head in the aqueous solution through flexible tubing with applied air pressure. The temperature of the prepolymer was maintained between about 50° C. and about 70° C. The extruded prepolymer stream was dispersed and chain-extended with water under the continuous mixing of about 5,000 rpm. In a period of about 50 minutes, a total amount of about 540 grams of prepolymer was introduced and dispersed in water. Immediately after the prepolymer was added and dispersed, the dispersed mixture was charged with about 2 grams of Additive 65 (commercially available from Dow Corning®, Midland Mich.). The reaction mixture was then mixed for about another 30 minutes followed by the addition of about 6 grams of diethylamine (DEA) and additional mixing. The resulting solvent-free aqueous dispersion was milky white and stable. The viscosity of the dispersion was adjusted with the addition and mixing of Hauthane HA thickening agent 900 (commercially available from Hauthway, Lynn, Mass.) at a level of about 2.0 wt % of the aqueous dispersion. The viscous dispersion was then filtered through a 40 micron Bendix metal mesh filter and stored at room temperatures for film casting or lamination uses. The dispersion had solids level of 43% and a viscosity of about 25,000 centipoises.

Example 7

Capped glycol prepolymer, formed from Terathane® 1800 glycol and Isonate® 125MDR (commercially available from the Dow Company, Midland, Mich.) and with a capping ratio of 1.688, was obtained from a commercial LYCRA® spandex production line. LYCRA® is INVISTA's registered trademark for spandex. This prepolymer of 300 grams was mixed with 150 grams of NMP solvent in a plastic bottle for 10 minutes to reduce the viscosity. The diluted mixture was poured into a steel tube to be injected into a stainless steel container for dispersing. The container had 2000 grams of de-ionized water, 30 grams of T DET N14 surfactant (commercially available from Harcros of Kansas City, Kans.) and 3 grams of ethylenediamine chain extender which were premixed and cooled to 5° C. The diluted prepolymer was injected under air pressure at about 40 psi through a tubing of ⅛ inch inner diameter, a high-speed laboratory disperser (model number, HSM-100LC commercially available from Charles Ross & Son Company of Hauppauge, N.Y.) was operated at 5000 rpm. The addition of diluted prepolymer was completed within 15 minutes, the formed milky dispersion was continued to disperse for additional 5 minutes. Back weighing of the container gave the total amount of diluted capped glycol added into the dispersion being 347 grams, equivalent to 231 grams of capped glycol prepolymer added into the dispersion. Additive 65 foam controlling agent of 3 grams (commercially from Dow Corning of Midland, Mich.) was added to the dispersion, and the dispersion was allowed for mixing at 5000 rpm for another 30 minutes before pouring into a plastic bottle.

The average particle size of the dispersion was determined to be 32.59 micron, with 95% of the particles below 65.98 microns, by the use of a Microtrac X100 particle size analyzer (Leeds, Northrup). The solid polymer particles was filtered using a Buchner funnel with Whatman® filter paper under reduced pressure, rinsed the filter cake with water for three times, and dried at 60-65° C. for 4 hours. The particles did not form into films during the filtration or drying. The dried filter cake was easily ground into fine powders with the use of a laboratory Waring® blender (Blender 700 Model 33BL79 manufactured by Dynamics Inc., New Hartford, Conn.). In commercial practice, the solid particles would be isolated directly from the dispersion using known drying processes such as spray drying. The dried powder had a weight average molecular weight of 352,550 and a number average molecular weight of 85,200 as determined by GPC.

Example 8

In Example 8 the same components and dispersion procedures were used as in Example 7, except that the solvent used to dilute the capped glycol prepolymer was changed to xylenes, and the amount of ethylenediamine chain extender was increased to 4.5 grams. Back weighing of the container gave the total amount of diluted capped glycol added into the dispersion being 339 grams, equivalent to 226 grams of capped glycol prepolymer added into the dispersion.

The average particle size of the dispersion was determined to be 22.88 micron, with 95% of the particles below 46.97 microns. The solid polymer particles do not form into films when isolated.

Example 9

In Example 9 the same components and dispersion procedures were used as in Example 7, except that the ethylenediamine chain extender was replaced by the same amount of a branched polyethylenimine (Mn about 600 by GPC from Aldrich). Back weighing of the container gave the total amount of diluted capped glycol added into the dispersion being 340 grams, equivalent to 227 grams of capped glycol prepolymer added into the dispersion.

The average particle size of the dispersion was determined to be 58.12 micron, with 95% of the particles below 258.5 microns. The solid polymer particles did not form into films when isolated.

Example 10

A glove box with dry nitrogen atmosphere was used to prepare the prepolymer. In two separate 2000 ml Pyrex® glass reaction kettles, which was equipped with an air pressure driven stirrer, a heating mantle and a thermocouple temperature measurement, each was charged with 220.0 grams of Terathane® 1800 glycol (commercially available from INVISTA) and 220.0 grams of Pluracol® HP 4000D glycol (commercially available from BASF). This glycol mixture was heated to 50° C. with stirring, followed by the addition of 75.03 grams of Isonate® 125MDR (commercially available from Dow Chemical). The reaction mixture was then heated to 90° C. with continuous stirring and held at 90° C. for 120 minutes. Samples were taken from the reactor, and determined to have 2.170 and 2.169% NCO respectively, as measured by the method of S. Siggia, "Quantitative Organic Analysis via Functional Group", 3rd Edition, Wiley & Sons, New York, pp. 559-561 (1963).

A 3000 ml stainless steel beaker was charged with 1600 grams of de-ionized water, 15 grams of T DET N14 surfactant (commercially available from Harcros of Kansas City, Kans.) and 5 grams of Additive 65 (commercially available from Dow Corning). This mixture was then cooled with ice/water to 10° C. and mixed with a high shear laboratory mixer with rotor/stator mix head (Ross, Model 100LC) at 5000 rpm for 30 seconds. The viscous prepolymers, as prepared above in two reactors, were poured into a metal tubular cylinder and was added to the bottom of the mix head in the aqueous solution through a flexible tubing with applied air pressure. The temperature of the prepolymer was maintained between 50-70° C. The extruded prepolymer stream was dispersed and chain-extended with water under the continuous mixing of 5000 rpm. In a period of 5 minutes, a total amount of 616 grams of prepolymer was introduced and dispersed in water. After the prepolymer was added and dispersed, the dispersed mixture was mixed for another 40 minutes. The resulting solvent-free aqueous dispersion was milky white to pale blue color, with 28.84 wt % solids content and 44 centipoises viscosity. The dispersion was cast on a sheet of polyethylene and dried in a fume hood for overnight under ambient conditions to form an elastic continuous film. By GPC measurement, this film had a weight average molecular weight of 127,900 and a number average molecular weight of 41,000.

Example 11

The procedures and conditions were essentially the same as above mentioned Example 10, except that the surfactant was changed to Bio-soft® N1-9 (commercially available from Stepan of Northfield, Ill.). A total of 640 grams of prepolymer, with 2.156 and 2.136% NCO from the two reactors, was dispersed into water. The formed solvent-free dispersion had a solids content of 26.12% and viscosity of 51 centipoises. The cast and dried elastic film had a weight average molecular weight of 133,900 and a number average molecular weight of 44,400.

Example 12

The solvent-free prepolymer, as prepared according to the procedures and composition described in Example 5, was used to make the polyurethaneurea aqueous dispersion of the present invention.

A 2,000 ml stainless steel beaker was charged with about 700 grams of de-ionized water, about 15 grams of sodium dodecylbenzenesulfonate (SDBS), and about 10 grams of triethylamine (TEA). This mixture was then cooled with ice/water to about 5° C. and mixed with a high shear laboratory mixer with rotor/stator mix head (Ross, Model 100LC) at about 5,000 rpm for about 30 seconds. The viscous prepolymer, prepared in the manner as Example 1 and contained in a metal tubular cylinder, was added to the bottom of the mix head in the aqueous solution through flexible tubing with applied air pressure. The temperature of the prepolymer was maintained between about 50° C. and about 70° C. The extruded prepolymer stream was dispersed and chain-extended with water under the continuous mixing of about 5,000 rpm. In a period of about 50 minutes, a total amount of about 540 grams of prepolymer was introduced and dispersed in water. Immediately after the prepolymer was added and dispersed, the dispersed mixture was charged with about 2 grams of Additive 65 (commercially available from Dow Corning®, Midland Mich.) and about 6 grams of diethylamine (DEA). The reaction mixture was then mixed for about another 30 minutes. The resulting solvent-free aqueous dispersion was milky white and stable. The viscosity of the dispersion was adjusted with the addition and mixing of Hauthane HA thickening agent 900 (commercially available from Hauthway, Lynn, Mass.) at a level of about 2.0 wt % of the aqueous dispersion. The viscous dispersion was then filtered through a 40 micron Bendix metal mesh filter and stored at room temperatures for film casting or lamination uses. The dispersion had solids level of 43% and a viscosity of about 25,000 centipoises. The cast film from this dispersion was soft, tacky, and elastomeric.

Example 13

Fabric Testing

Compositions of the present invention were tested in combination with cotton/LYCRA® fabric (97% cotton/3% LYCRA® spandex). The control for this example was fabric washed with non-concentrated Confort™ fabric softener by Unilever. Each of the compositions as shown in Table 1, were used with the cotton/LYCRA® fabric by washing with Ariel™ liquid detergent available from Procter and Gamble on program 4 at 40° C. on a Schulthess® programmable automatic washing machine using standard load fabric to reach 2.5 kg load and rinsing with 18 g of the fabric softener composition. After tumble drying, the fabrics were evaluated for any deposit on the surface. None of the three fabrics showed any deposition of powder or film.

The compositions in Table 1 are as follows:
(a) Fabric treated with fabric softener only (control)
(b) Fabric treated with fabric softener, 1% wt of the dispersion of example 6, a film forming anionic polyurethaneurea water, and 2% wt of Unimer (synthetic wax to improved dispersion)
(c) Fabric treated with fabric softener, 1% wt of the polyurethaneurea powder of example 5, and 2% wt of Unimer (synthetic wax to improved dispersion).

Mixing of the compositions (b) and (c) including the fabric softener delivered a homogeneous dispersion (no sedimentation, nor agglomeration).

Each fabric was evaluated for easy care. Standard test method AATCC TM 124/ISO 15487 was used to determine the durable press rating ("Drating") before and after ironing. "Drating" is a measure of the three-dimensional smoothness of the fabric. Iron gliding or ease of ironing was measured as the time for the iron to glide over a given length of fabric with the ironing board at an angle of approximately 20°.

The easy care results are shown in Table 1.

TABLE 1

| | Easy Care | | |
| Fabric | DP Rating before ironing | DP rating after ironing | ease of ironing (s) |
| --- | --- | --- | --- |
| (a) | 1 | 1.5 | 5 |
| (b) | 1.5 | 2.5 | 3.5 |
| (c) | 1.5 | 2.5 | 3 |

From the results in Table 1, it is shown that both fabrics treated with powder or dispersion show a better improvement of DP rating (1 point gained after ironing) as compared to the control (0.5 point gained after ironing).

Also the fabrics (b) and (c) treated with the compositions of the present invention show a faster gliding of the iron on the fabric surface.

The compositions (a), (b), and (c) were also evaluated for perfume/fragrance substantiation. Three people were allowed separately to smell each of the fabrics. Each of these people observed a stronger fragrance in the treated fabrics (b) and (c) which were treated with the compositions of the present invention.

Absorption properties (moisture management) of fabrics including those treated with the compositions of the present invention have also been tested. These properties were measured to demonstrate the differences of fabrics after treatment with the powders or dispersions of the present invention as compared to untreated fabrics.

For each of the fabrics (a), (b), and (c) as described above, one drop (approximately 30 micro liters) each of linseed oil and water was applied to the surface of the fabric. The time until complete absorption of each droplet was measured and reported in seconds (s) in Table 2. The area of the drop surface at 60 seconds following complete absorption by the fabric was also measured and reported as square centimeters ($cm^2$) in table 2.

TABLE 2

| | Moisture Management | | | |
|---|---|---|---|---|
| | absorbtion time (s) | | planar wicking ($cm^2$) | |
| | water | oil | water | oil |
| (a) | 138 | 434 | 7.28 | 7.56 |
| (b) | 105 | 382 | 4.64 | 6.75 |
| (c) | 81 | 320 | 4.50 | 6.41 |

As shown in Table 2, the dispersion (b) and powder (c) of the present invention offered improvement in comparison to the control (a) with respect to absorption. The use of the powder form (c) showed significant improvement.

Example 14

100% Cotton Woven Fabric Testing

A 100% cotton woven fabric was also tested after treatment with a composition of the some embodiments. The control for this example was a concentrated fabric softener, Softlan™ Ultra by Colgate Palmolive. Each of the compositions as shown in Table 3, were used with 100% cotton fabric by washing with Ariel™ liquid detergent on program 4 at 40° C. on a Schulthess® programmable automatic washing machine using standard load fabric to reach 2.5 kg load and rinsing with 18 g of the fabric softener composition. After tumble drying (at moderate temperature), the fabrics were evaluated for any deposit on the surface. Neither of the fabrics showed any deposition of powder or film.

The compositions in Table 3 are as follows:
(e) Fabric treated with fabric softener only (control)
(f) Fabric treated with fabric softener and 10% wt of the dispersion of example 10, a non-ionic polyurethaneurea dispersion Mixing of the composition (f) including the fabric softener delivered a homogeneous dispersion (no sedimentation, nor agglomeration).

In order to test the fabrics for growth, first the available stretch or maximum stretch was calculated. The available stretch was determined by first conditioning a fabric specimen followed by cycling three times on a constant-rate-of-extension tensile tester between 0-30N. The maximum stretch was calculated by the following formula:

Maximum stretch %=$(ML-GL) \times 100/GL$ where: ML is the length in mm at 30N; and
GL is the gauge length of 250 mm.

Separate specimens of each fabric were then extended to 80% of the "available stretch" and held for about 30 min. The fabric specimens were then allowed to relax for about 60 min. and growth was measured and calculated. According to:

Growth %=$L2/L \times 100$ where: "growth" is recorded as a percent after relaxation;
L2=the increased length in cm after relaxation; and
L=the original length in cm.

Each of the fabrics (e) and (f) were measured for fabric growth.

The results are shown in Table 3:

TABLE 3

| Fabric Growth (weft direction) | |
|---|---|
| fabric | growth (%) |
| (e) | 7.4 |
| (f) | 5.8 |

Fabric growth is a measure of shape retention. Growth values represent the un-recovered elongation during wear. A lower value in growth demonstrates that the fabric has a better ability to recover its initial shape.

Fabrics (e) and (f) were also tested for difference in release of perfume after a washing and rinsing cycle. One to two grams of each fabric sample was placed in a sealed gas sampling vessel. Fabric stressing was conducted by shaking with steel ball bearings. The volatile compounds released from the sample were drawn out of the headspace of the gas sampling vessel through a Tenex™ sampling tube using a gas sampling pump operating at 50 cc per minute for 20 minutes. The Tenex™ tube trapped the volatile organic compounds (VOC) for analysis. The Tenex™ tube was then thermally desorbed with the volatile organics directed into a GC/MS for analysis. The results of the VOC measures in Table 3a show that more perfume released from the fabric rinsed with the fabric softener which contains the dispersion of example 10, a non-ionic polyurethaneurea dispersion TABLE 3a

| VOC testing | |
|---|---|
| Fabric | Volatile concentration ng/L/g |
| (e) | 7 |
| (f) | 48 |

Example 15

Spandex/Cotton Blend Fabric Testing

A spandex/cotton blend woven fabric was also tested after treatment with a composition of the some embodiments. The control for this example was a concentrated fabric softener, Softlan™ Ultra by Colgate Palmolive. Each of the compositions as shown in Table 4, were used with cotton/spandex blend fabric by washing with Ariel™ liquid detergent on program 4 at 40° C. on a Schutless® programmable automatic washing machine using standard load fabric to reach 2.5 kg load and rinsing with 18 g of the fabric softener composition. After tumble drying (at moderate temperature), the fabrics were evaluated for any deposit on the surface. Neither of the fabrics showed any deposition of powder or film.

The compositions in Table 4 are as follows:
(g) Fabric treated with fabric softener only (control)
(h) Fabric treated with fabric softener and 10% wt of the dispersion of example 10, a non-ionic polyurethaneurea dispersion Mixing of the composition (h) including the fabric softener delivered a homogeneous dispersion (no sedimentation, nor agglomeration). Each of the fabrics (g) and (h) were measured for fabric growth.

The results are shown in Table 4:

TABLE 4

Fabric Growth (weft direction)

| fabric | growth (%) |
|---|---|
| (g) | 4.8 |
| (h) | 3.8 |

Fabric growth is a measure of shape retention. Growth values represent the un-recovered elongation during wear. A lower value in growth demonstrates that the fabric has a better ability to recover its initial shape.

Two LYCRA® spandex/cotton blend fabrics were also tested after treatment with a composition of some embodiments. The control for this example was a concentrated fabric softener, Soupline™ Ultra by Colgate Palmolive. Each of the compositions as shown in Tables 4a and 4b, were used with cotton and LYCRA® spandex blend fabric by washing with Dixan® gel detergent available from Henkel Corporation at 40° C. with standard program on a Miele™ commercial washing, using standard load fabric to reach 2.5 kg load and rinsing with 30 ml of fabric softener composition. After tumble drying (at moderate temperature), the fabrics were evaluated for any deposit on the surface. Neither of the fabrics showed any deposition of powder or film. For the fabrics below, CK is a circular knitted fabric with 95% cotton-5% LYCRA® spandex and WOV is a gray weft stretch woven fabric, with 97% cotton-3% LYCRA® spandex.

The compositions in Table 4a and 4b are as follows:
(i) fabric treated with fabric softener only (control-CK)
(j) fabric treated with fabric softener and 10% wt (3% active ingredient) of the dispersion of example 10, a non-ionic polyurethaneurea dispersion (treated-CK)
(k) fabric treated with fabric softener only (control-WOV)
(l) fabric treated with fabric softener and 10% wt (3% active ingredient) of the dispersion of example 10, a non-ionic polyurethaneurea dispersion (treated-WOV)

TABLE 4a

Fabric growth CK

| fabric | Growth (%) |
|---|---|
| (i) length direction | 7.5 |
| (j) length direction | 7.2 |
| (i) width direction | 6.9 |
| (j) width direction | 6.4 |

TABLE 4b

Fabric growth WOV

| fabric | Growth % |
|---|---|
| (k) weft direction | 7.29 |
| (l) weft direction | 6.97 |

Example 16

Paint Anti-skid

Compositions of some embodiments were tested for "anti-skid" properties. These tests were completed according to ASTM D4518-91 with modification as described below. The paint tested (which was also the control) is a solvent free matte white vinyl acetate base paint commercially available from Akzo Nobel. Compositions and average particle sizes as shown in the table below were added with the goal of increase static friction. The results are the coefficient of static friction as calculated according to the test method and shown in Table 5.

The procedure for measurement of static friction on coated surface was done to determine the resistance to sliding on a coated surface (paint) by measuring the static friction. For each paint sample, a paint layer was prepared by application with a paint roller. The paint included particles as shown in Table 5. The paint was then allowed to dry for one day. This was followed by the application of a second layer of paint which was allowed to dry for one day.

ASTM D4518-91 was modified by using a rounded edge aluminum block instead of a steel block with the same weight and polished surface. The block was placed on the painted surface on an inclined plane. Between measurements, the aluminum block was cleaned with acetone.

To obtain the same constant speed for the inclination of the plane, an INSTRON dynamometer was used with the following program:

Absolute ramp-0 to 300% extension at 480 mm/min (~1.5+/−0.5°/s)

Kevlar yarn was used to avoid yarn extension and provide good reproducibility.

The angle of inclination (a) was calculated by trigonometry based on the height of the plane (h) and the length of the plane (X), which was 30 cm. The coefficient of static friction was measured as:

Static friction=tan a; and
Static friction=tan(sin$^{-1}$ h/X)

TABLE 5

Friction testing

| | 10% wt | 5% wt |
|---|---|---|
| control | 0.314 | 0.289 |
| Softsand ®* 100 μm | 0.390 | 0.328 |
| Polyurethaneurea flock | 0.386 | 0.378 |
| Example 2 (polyurethaneurea powder) 90 μm | 0.361 | 0.353 |
| Example 7 (polyurethaneurea powder) 19 μm | 0.346 | 0.381 |
| Example 1 (polyurethaneurea powder) 100 μm | 0.354 | 0.375 |
| Nylon flock | | 0.392 |

*Softsand is a rubber texturizing agent commercially available from Soft Point Industries, Copley, OH.

Table 5 demonstrates that the polymer compositions of some embodiments provide comparable or superior anti-skid properties as compared to the control or to the rubber texturizing agent. Superior results are noted for all inventive compositions at the 5% additive level.

Example 17

Paint Cracking

Testing for flexibility of paint compositions was conducted based on BS EN ISO 6860:1995. Paint compositions were prepared as shown in Table 6 including a commercially available matte white base paint from Akzo Nobel. Each paint was coated to a thickness of approximately 30 mils on a cardboard substrate. Then each substrate was folded over a conical mandrel to determine the minimum bending diameter that was achieved without cracking of the paint.

As can be seen from the results in Table 6, there is significant flexibility of the paints including the dispersions of some embodiments.

TABLE 6

Paint cracking testing

| Addition | minimum bending diameter without cracks (mm) |
|---|---|
| None (control) | >24 |
| 5% wt dispersion of Example 12 | 12 |
| 5% wt dispersion of Example 6 | 15 |

Example 18

Elongation at Break and Young's Modulus

Samples of paint were mixed according to the compositions described in Tables 7 and 8. The paint compositions were coated on a releasable substrate to form films. Samples were cut from these films that were of 1 cm width and 5 cm length for each sample. Three films were tested for each composition using an Instron® dynamometer. Initial tests were done to measure the elongation and force at break for each material. From this data, the constrain and the Young's modulus (or module of elasticity) were calculated. The results are shown in Table 7 and 8.

TABLE 7

Elongation at Break

| Paint composition | Break elongation % Sample | | | |
|---|---|---|---|---|
| | 1 | 2 | 3 | average |
| Paint 1 - control | 1.32 | 1.62 | 1.94 | 1.63 |
| Paint 1 + 5% wt dispersion of Example 12 | 1.76 | 1.55 | 1.83 | 1.71 |
| Paint 1 + 5% wt dispersion of Example 6 | 1.69 | 1.62 | 1.43 | 1.58 |
| Paint 1 + 50% wt dispersion of Example 12 | 51.50 | 41.03 | 38.33 | 43.62 |
| 100% dispersion of Example 12 | 198.77 | 126.20 | 176.90 | 167.29 |
| 100% dispersion of Example 6 | >300 | 266.60 | | >300 |
| Paint 2 - control | 188.23 | 185.30 | 176.43 | 183.32 |
| Paint 2 + 5% wt dispersion of Example 12 | 200.40 | 201.40 | 177.00 | 192.93 |
| Paint 2 + 5% wt dispersion of Example 6 | 174.13 | 164.63 | 200.10 | 179.62 |
| Paint 3 - control | 3.19 | 3.09 | 3.12 | 3.13 |
| Paint 3 + 5% wt dispersion of Example 12 | 3.54 | 2.87 | 2.19 | 2.87 |
| Paint 3 + 5% wt dispersion of Example 6 | 3.83 | 2.80 | 2.87 | 3.17 |

Paint 1 - matte white solvent free commercially available from Akzo Nobel
Paint 2 - acrylic emulsion clear gloss paint commercially available from Akzo Nobel
Paint 3 - acrylic emulsion matte white paint commercially available from Akzo Nobel

TABLE 8

Young's Modulus

| Paint composition | Young's modulus (N/mm2) Sample | | | |
|---|---|---|---|---|
| | 1 | 2 | 3 | average |
| Paint 1 - control | 1086.56 | 1097.16 | 1139.03 | 1107.58 |
| Paint 1 + 5% wt dispersion of Example 12 | 762.36 | 648.53 | 714.56 | 708.48 |
| Paint 1 + 5% wt dispersion of Example 6 | 590.19 | 743.91 | 577.56 | 637.22 |
| Paint 1 + 50% wt dispersion of Example 12 | 20.73 | 25.72 | 26.06 | 24.17 |
| 100% dispersion of Example 12 | 3.66 | 4.05 | 4.00 | 3.90 |
| 100% dispersion of Example 6 | 2.60 | 4.26 | 3.61 | 3.49 |
| Paint 2 - control | 0.55 | 0.57 | 0.52 | 0.55 |
| Paint 2 + 5% wt dispersion of Example 12 | 0.49 | 0.52 | 0.54 | 0.52 |
| Paint 2 + 5% wt dispersion of Example 6 | 0.49 | 0.52 | 0.48 | 0.50 |
| Paint 3 - control | 709.92 | 694.21 | 645.91 | 683.35 |
| Paint 3 + 5% wt dispersion of Example 12 | 629.13 | 606.13 | 634.43 | 623.23 |
| Paint 3 + 5% wt dispersion of Example 6 | 629.02 | 606.13 | 534.91 | 590.02 |

Paint 1 - matte white solvent free commercially available from Akzo Nobel
Paint 2 - acrylic emulsion clear gloss paint commercially available from Akzo Nobel
Paint 3 - acrylic emulsion matte white paint commercially available from Akzo Nobel As can be seen from Tables 7 and 8, the inventive compositions showed improvement over the control, which was the base paint. Specifically, the inventive compositions had a lower Young's modulus which indicates higher material elasticity.

Example 19

Elongation

Each of three paint samples including the dispersions of some embodiments were also tested to determine the maximum elongation at 4N for paints 1 and 3 and 1N for paint 2 at the $3^{rd}$ cycle using an Instron® dynamometer. The maximum force was chosen from the previous elongation test as set forth in Example 18, in order to be in the elastic domain of the material (flat zone of the stress strain curve). The testing was to measure the difference in elongation when same force is applied. The results are shown in Table 9.

TABLE 9

Elongation 3rd cycle

| | Average max. elongation 3rd cycle % |
|---|---|
| Paint 1 - control | 0.60 |
| Paint 1 + 5% wt dispersion of Example 12 | 1.45 |
| Paint 1 + 5% wt dispersion of Example 12 | 1.44 |
| Paint 2 - control | 40.13 |
| Paint 2 + 5% wt dispersion of Example 12 | 102.00 |
| Paint 2 + 5% wt dispersion of Example 6 | 129.58 |
| Paint 3 - control | 0.93 |
| Paint 3 + 5% wt dispersion of Example 12 | 2.49 |
| Paint 3 + 5% wt dispersion of Example 6 | 3.29 |

Paint 1 - matte white solvent free commercially available from Akzo Nobel
Paint 2 - acrylic emulsion clear gloss paint commercially available from Akzo Nobel
Paint 3 - acrylic emulsion matte white paint commercially available from Akzo Nobel Table 9 demonstrates that the addition of the inventive polyurethaneurea dispersions improved the elongation properties of all three base paints. At a minimum, the elongation of the base paint is doubled after the addition of the inventive dispersions.

Example 20

Oil and Water Absorption-Time

In order to test the absorption properties of inventive powder compositions in comparison to commercially available powder compositions, several compositions were tested to determine the time required for the absorption of a drop each of linseed oil, water and artificial perspiration. In each of the tests, a drop of linseed oil, water, or artificial perspiration was placed on each of the inventive and commercially available powders. The time until absorption of the drop was noted as shown Table 10.

TABLE 10

Time for Absorption

| sample | average particle size μm | Linseed oil sec | Water sec | Artificial Perspiration sec |
|---|---|---|---|---|
| Nylon Powder[1] | 20 | 377 | —[5] | —[5] |
| Silica[2] | 12 | 750 | 28 | 25 |
| Talc[6] | 14-18 | 52 | 2700 | |
| BPD-500[2] | 12 | 54 | 9 | 7 |
| BPD-800[2] | 6 | 75 | 18 | 15 |
| Powder of Example 7 | 19 | 37 | 38 | 38 |
| Powder of Example 1 | 90 | 14 | 3 | 2 |
| Powder of Example 1 | 77 | 10 | 3 | |
| Powder of Example 1[3] | 34 | 12 | 9 | |
| Powder of Example 1[4] | 33 | 23 | 3 | |

[1]Nylon 6 powder commercially available from Arkema
[2]Polyurethane powder commercially available from KOBO
[3]Spun dyed with green pigment
[4]Spun dyed with blue pigment
[5]Sample unable to absorb on its own
[6]Ultra Talc 2000 commercially available from KISH As shown in Table 10, the inventive powders provided a faster absorption time for oil and water as compared with the nylon and silica and provided similar or improved absorption time as compared with the commercially available polyurethane powders.

Example 21

Oil and Water Absorption-Mass

In order to test the absorption properties of inventive powder compositions in comparison to commercially available powder compositions, several compositions were tested to determine the mass of either linseed oil, water and artificial perspiration, which was absorbed according to Test method ASTM D281-95 (modified for water and artificial perspiration). The results are shown in Table 11.

TABLE 11

Mass of Absorption

| sample | Average particle size μm | Linseed oil g/g | Water g/g | Artificial Perspiration g/g |
|---|---|---|---|---|
| Nylon Powder[1] | 20 | 0.69 | 0.82 | 0.84 |
| Silica[2] | 12 | 1.05 | 1.10 | 1.16 |
| Talc[5] | 14-18 | 0.46 | 0.55 | |
| BPD-500[2] | 12 | 0.54 | 0.63 | 0.67 |
| BPD-800[2] | 6 | 0.64 | 0.74 | 0.77 |
| Powder of Example 7 | 19 | 0.68 | 0.68 | 0.66 |
| Powder of Example 1 | 90 | Not performed | Not performed | 0.94 |
| Powder of Example 1 | 77 | 1.49 | 1.18 | |
| Powder of Example 1[3] | 34 | 1.55 | 1.30 | |
| Powder of Example 1[4] | 33 | 1.08 | 1.11 | |

[1]Nylon 6 powder commercially available from Arkema
[2]Polyurethane powder commercially available from KOBO
[3]Spun dyed with green pigment
[4]Spun dyed with blue pigment
[5]Ultra Talc 2000 commercially available from KISH As shown in Table 11, the inventive compositions were able to absorb as well as or better than the commercially available powders.

Example 22

Exfoliating Compositions

Incorporating physical exfoliants into cosmetic cleansing preparations is increasingly popular. Early products relied on the abrasive effect of broken nut shells in standard cosmetic bases and were as appealing to the consumer as sandpaper. Currently, there are many exfoliants available to the cosmetic chemist from both natural and synthetic sources. The particle size and abrasive qualities of each type can be strictly controlled enabling the desired level of exfoliation to be precisely formulated and a better understanding of rheological properties enables stable, elegant products to be made with the exfoliant distributed evenly throughout.

Polyethylene (PE) Spheres are some of the most common polymer exfoliating agents: they are available in different size range. Commercial samples of Polyethylene (PE) Spheres are available from A&E Connock (Perfumery & Cosmetics) Ltd, in the following grades:
   65/100 mesh size (approx 150-230 μm),
   35/48 mesh size (approx 300-500 μm),
   24/32 mesh size (approx 600-700 μm),
   14/16 mesh size (approx 1200-1400 μm).

The following polyureaurethane powders with the following particle sizes have been prepared to compare with PE spheres:
Polyurethane urea powders prepared by Roach's process: 25-200 μm
   Polyurethaneurea powders of Example 7: 300-800 μm
   Polyurethaneurea powders of Example 3: 500-1000 μm
Each powder was added at 15% by weight to a shower gel (Silk Glow Softening Silk Shower by Dove) and compared with an already made exfoliating product which contains oxidized polyethylene as exfoliating agent (Silk Glow Douche Gommage Quotidienne Soie by Dove).

The compositions with Polyurethane urea powders prepared by Roach's process did not provide any real peeling effect, as the particle size of the powder is too small. By comparison, the powders of Examples 3 and 7 mixed nicely with the shower gel and delivered an exfoliating effect. Because of the compressibility of the polyurethaneurea powders, they have a much softer touch and deliver a much gentler peeling effect on the skin.

Example 23

Film Forming Polymers

In the cosmetic industry, many film forming polymers are used, especially in nail polish, mascara-eye liners, face make up, sunscreen products and hair care formulations.

The chemical composition can vary from acrylate copolymers, polyurethane, polyvinylpyrrolidone vinyl acetate, polyacrylic acid (carbomer). These can be used as styling polymer or as thickeners and provide transparent flexible films with different level of gloss, adhesion, abrasion resistance and flexibility. The polyurethaneurea water borne dispersions of Examples 5, 6 and 10 can also be used to provide these effects.

The great advantage of these compositions will be the improved elasticity and flexibility, the soft and pleasant touch and the good abrasion resistance. Two polyurethane polymer dispersions, commercially available from Noveon: Avalure® UR 425 and UR 450 were tested and compared to the polyurethaneurea compositions as described herein.

Films were cast at 20 mil thickness for the commercially available dispersions as well as the dispersion of example 6. These were compared for elastic properties which are shown in Table 12.

TABLE 12

Elastic Properties of Films

| | max. elongation at break % average | max. constraint at break (N/mm2) | Young's modulus (N/mm2) average |
|---|---|---|---|
| UR425 | 426.00 | 13.08 | 41.11 |
| UR450 | 210.00 | 12.98 | 128.97 |
| Dispersion of Example 6 | 443.50 | 7.20 | 6.18 |

The Dispersion of Example 6 clearly exhibits a very elastic behavior in comparison to the commercially available materials, as the Young modulus is much lower. This dispersion will allow high formula elasticity and will better follow the movements of the skin.

Example 24

Extruded Article

Nylon 12 pellets commercially available from Sigma Aldrich were used for the extrusion. The nylon 12 pellets were dried overnight to remove any residual water. A blend of nylon 12 pellets (252 g) and the polyurethaneurea powder of Example 1 (80 g) were combined in a plastic bag and combined by manual agitation to achieve visual uniformity. This mixture was then placed in an aluminum bag to prevent moisture contamination. The mixture was then extruded at a temperature of about 200° C. to provide a sheet of the mixed material of about 1 cm width and about 1-2 mm thickness.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. An article with improved shock resistance, flexibility and shape retention, said article formed by:
   (a) preparing a polyurethane composition in the form of a first mixture comprising:
      i) powder and flock or
      ii) beads and flock or
      iii) powder, beads, and flock;
   (b) combining said first mixture with a thermoplastic polymer, wherein the thermoplastic polymer is selected from the group consisting of polyethylene, polycarbonate, polyvinyl chloride (PVC), polymethacrylate, and combinations thereof, to form a second mixture; and
   (c) extruding or molding said second mixture in the form of said article.

2. The article of claim 1, wherein said thermoplastic polymer is polycarbonate.

* * * * *